United States Patent
DeGeorge et al.

(10) Patent No.: US 7,905,926 B2
(45) Date of Patent: Mar. 15, 2011

(54) METHODS AND KITS FOR PERMANENTLY COLORING HAIR

(75) Inventors: Michael DeGeorge, Middletown, NJ (US); Jeremy Puco, Budd Lake, NJ (US); Delphine Allard, Westfield, NJ (US); Gilles Genain, Paris (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 12/667,481

(22) PCT Filed: Jul. 3, 2008

(86) PCT No.: PCT/IB2008/002719
§ 371 (c)(1),
(2), (4) Date: Feb. 15, 2010

(87) PCT Pub. No.: WO2009/010883
PCT Pub. Date: Jan. 22, 2009

(65) Prior Publication Data
US 2010/0192969 A1 Aug. 5, 2010

Related U.S. Application Data

(60) Provisional application No. 60/947,744, filed on Jul. 3, 2007.

(51) Int. Cl.
*A61Q 5/10* (2006.01)

(52) U.S. Cl. ............. 8/405; 8/406; 8/410; 8/412; 8/426; 132/202; 132/208

(58) Field of Classification Search ............. 8/405, 406, 8/410, 426; 132/202, 208
See application file for complete search history.

(56) References Cited

U.S. PATENT DOCUMENTS

| | | | |
|---|---|---|---|
| 3,472,604 A | 10/1969 | Prota et al. | |
| 4,104,021 A | 8/1978 | Lapidus et al. | |
| 5,374,288 A | 12/1994 | Prota et al. | |
| 6,736,860 B2 * | 5/2004 | Patel et al. | ............ 8/405 |
| 2005/0193501 A1 | 9/2005 | Chan et al. | |
| 2006/0265818 A1 | 11/2006 | Seiler et al. | |

FOREIGN PATENT DOCUMENTS

| | | |
|---|---|---|
| CN | 101259087 A | 9/2008 |
| DE | 19721785 C1 | 9/1998 |
| EP | 0146350 A2 | 6/1985 |
| GB | 200375 A | 7/1923 |
| JP | 3-258714 A | 11/1991 |
| JP | 2002-137916 A | 5/2002 |

* cited by examiner

*Primary Examiner* — Eisa B Elhilo
(74) *Attorney, Agent, or Firm* — Connolly Bove Lodge & Hutz LLP

(57) ABSTRACT

Disclosed are methods and kits for coloring the hair involving a color base composition comprising at least one primary dye intermediate, and a developer composition comprising an oxidizing agent chosen from persulfates, perborates, percarbonates, and mixtures thereof. Preferably, the color base composition and developer composition are substantially free of an oxidation catalyst.

19 Claims, No Drawings

METHODS AND KITS FOR PERMANENTLY COLORING HAIR

CROSS REFERENCE TO RELATED APPLICATIONS

This application is a national phase of PCT/IB2008/002719, filed on Jul. 3, 2008 which claims priority to U.S. Provisional Application No. 60/947,744 filed Jul. 3, 2007, the entire contents of all are hereby incorporated by reference.

BACKGROUND OF THE INVENTION

Imparting a color change or color effect on hair can be done using permanent and semi-permanent or temporary hair coloring products. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents. Such permanent hair color products also contain ammonia or other alkalizing agents such as monoethanolamine (MEA) which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

It is also known that it is possible to vary the shades obtained with the primary intermediates by combining them with couplers or coloration modifiers. The variety of molecules used as primary intermediates and couplers can allow a wide range of colors to be obtained.

The artificial color of hair treated with a permanent hair coloring product does not easily wash out during the course of routine shampooing. The colorations obtained show good longevity (also referred to as color-fastness) with exposure to shampoo.

It has been surprisingly found that by employing a method of coloring keratinous substrates involving the steps of applying a color base composition containing at least one primary dye intermediate onto hair, followed by application of a developer composition containing at least one oxidizing agent chosen from persulfates, perborates, percarbonates, and salts thereof, onto the hair, either immediately after, or at any time thereafter that is convenient to the consumer from the time of application of the color base composition, for example up to 60 minutes thereafter, the following several significant advantages can be realized, as compared to the use of conventional permanent dyeing techniques: shorter dyeing time; comparable color-fastness to conventional permanent hair dyeing methods using peroxide developers; improved color deposit on the hair; little to no odor. In some instances, depending on the oxidative dye and/or coupler molecule used, different colors/shades may be obtained compared to the conventional hair coloring compositions/methods using peroxide developers.

Another disadvantage associated with the use of conventional permanent hair dye formulations and systems is that they are very messy to apply and have a tendency to cause scalp staining.

Thus, it is also an object of the present invention to provide a means of permanently coloring hair in a less messy or more clean manner.

Another object of the invention is to provide a permanent hair coloring system that does not lift the color of the hair, that is, it does not lighten hair color but is still able to vary the tone of the hair color or make the hair color darker. Lifting is defined as the process by which the natural hair melanin is removed. The alkaline environment ensures that the cuticles of the hair are opened to allow penetration of an oxidizing agent, such as hydrogen peroxide. Such an oxidizing agent breaks down the melanin by providing it with oxygen, and the melanin molecule is colorless when oxidized. This leaves the hair lightened from its natural color.

Another object of the present invention is to provide a means of permanently coloring hair in the absence of peroxide raw material ingredient.

BRIEF SUMMARY OF THE INVENTION

The present invention is directed to a method of permanently coloring hair involving the steps of:
  (a) providing a color base composition containing at least one primary dye intermediate chosen from ortho aminophenols, para aminophenols, ortho phenylenediamines, para phenylenediamines, double bases, heterocyclic bases, the acid addition salts thereof, and mixtures thereof;
  (b) applying the color base composition onto the hair;
  (c) optionally, rinsing the color base composition from the hair;
  (d) providing a developer composition containing at least one oxidizing agent chosen from persulfates, perborates, percarbonates, their salts, and mixtures thereof; and
  (e) applying the developer composition onto the hair in order to develop color, in situ, in the hair to form colored hair.
  The method of the present invention generally comprises at least one further step (f) of rinsing of the developer composition from the hair.
  According to a preferred embodiment, the color base composition and the developer composition are each substantially free of any oxidation catalyst.

The present invention is also directed to a kit for permanently coloring hair, the kit containing:
  (a) a multi-unit receptacle;
  (b) at least one unit comprising a color base composition containing at least one primary dye intermediate chosen from ortho aminophenols, para aminophenols, ortho phenylenediamines, para phenylenediamines, double bases, heterocyclic bases, the acid addition salts thereof, and mixtures thereof; and
  (c) at least one unit comprising a developer composition containing at least one oxidizing agent chosen from persulfates, perborates, percarbonates, their salts, and mixtures thereof.
  According to a preferred embodiment, the color base composition and the developer composition are each substantially free of any oxidation catalyst.
  It should be noted that by varying the pH of the system, different levels of color vibrancy can be achieved.

DETAILED DESCRIPTION OF THE INVENTION

Other than in the operating examples, or where otherwise indicated, all numbers expressing quantities of ingredients or reaction conditions are to be understood as being modified in all instances by the term "about".

As used herein, the expression "at least one" means one or more and thus includes individual components as well as mixtures/combinations.

As used herein, the term "applying" means contacting the hair to be dyed with the dye composition or with at least one of the compositions of the invention.

As used herein, "cosmetically acceptable" means that the item in question is compatible with any human keratin material and in particular human keratinous fibers, such as human hair.

As used herein, "conditioning" means imparting to at least one keratinous fiber at least one property chosen from combability, manageability, moisture-retentivity, luster, shine, and softness. In case of combing, the level of conditioning is evaluated by measuring, and comparing, the ease of combability of the treated hair and of the untreated hair in terms of combing work (gm-in).

As used herein, "formed from," means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

As used herein, the term "rheology modifier" means any compound capable of giving a viscosity to the oxidizing composition such that, once it is applied onto keratin fibres, this composition does not run, and remains perfectly localized at the point of application.

Color Base Composition

In this invention, the color base composition may contain a wide variety of oxidation dye precursors. These include primary dye intermediates and couplers.

A. Primary Dye Intermediates

Suitable primary dye intermediates include ortho or para aminophenols, ortho or para phenylenediamines, double bases, heterocyclic bases, and the acid addition salts thereof.

The para-phenylenediamines which can be used in the context of the invention can be chosen in particular from the compounds of the following formula (I) and their addition salts with an acid:

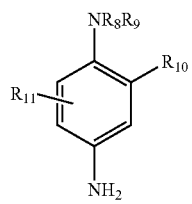

(I)

in which:

$R_8$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical, a $C_1$-$C_4$ alkyl radical substituted by a nitrogenous group, a phenyl radical or a 4'-aminophenyl radical;

$R_9$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical or a $C_1$-$C_4$ alkyl radical substituted by a nitrogenous group;

$R_8$ and $R_9$ can also form, with the nitrogen atom which carries them, a 5- or 6-membered nitrogenous heterocycle optionally substituted by one or more alkyl, hydroxyl or ureido groups;

$R_{10}$ represents a hydrogen atom, a halogen atom, such as a chlorine atom, a $C_1$-$C_4$ alkyl radical, a sulpho radical, a carboxyl radical, a $C_1$-$C_4$ monohydroxyalkyl radical, a $C_1$-$C_4$ hydroxyalkoxy radical, a $C_1$-$C_4$ acetylaminoalkoxy radical, a $C_1$-$C_4$ mesylaminoalkoxy radical or $C_1$-$C_4$ carbamoylaminoalkoxy radicals;

$R_{11}$ represents a hydrogen atom, a halogen atom or a $C_1$-$C_4$ alkyl radical.

Mention may in particular be made, among the nitrogenous groups in the above formula (I), of the amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Mention may more particularly be made, among the para-phenylenediamines of above formula (I), of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-methyl-1-N-(β-hydroxyethyl)-para-phenylenediamine and their addition salts with an acid.

Preference is very particularly given, among the para-phenylenediamines of above formula (I), to para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and their addition salts with an acid.

Among the ortho-phenylenediamines, mention may be made of N1-(2-hydroxyethyl)-4-nitro-o-phenylenediamine, 4-methyl-o-phenylenediamine, and 4-nitro-o-phenylenediamine and acid addition salts thereof.

As used herein, the term double bases means compounds comprising at least two aromatic nuclei having at least one of amino and hydroxyl groups.

Mention may in particular be made, among the double bases which can be used as oxidation bases in the composition in accordance with the invention, of the compounds corresponding to the following formula (II) and their addition salts with an acid:

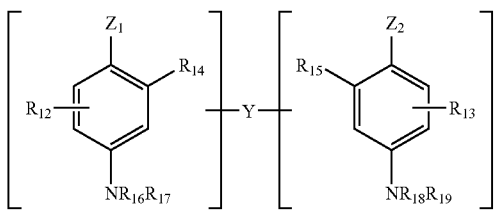

(II)

in which:
- $Z_1$ and $Z_2$, which are identical or different, represent a hydroxyl or $—NH_2$ radical which can be substituted by a $C_1$-$C_4$ alkyl radical or by a connecting arm Y;
- the connecting arm Y represents a linear or branched alkylene chain comprising from 1 to 14 carbon atoms which can be interrupted or terminated by one or more nitrogenous groups and/or by one or more heteroatoms, such as oxygen, sulphur or nitrogen atoms, and which is optionally substituted by one or more hydroxyl or $C_1$-$C_6$ alkoxy radicals;
- $R_{12}$ and $R_{13}$ represent a hydrogen or halogen atom, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical or a connecting arm Y;
- $R_{14}$, $R_{15}$, $R_{16}$, $R_{17}$, $R_{18}$ and $R_{19}$, which are identical or different, represent a hydrogen atom, a connecting arm Y or a $C_1$-$C_4$ alkyl radical;

it being understood that the compounds of formula (II) only comprise a single connecting arm Y per molecule.

Mention may in particular be made, among the nitrogenous groups of the above formula (II), of the amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Mention may more particularly be made, among the double bases of above formula (II), of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine, 1,8-bis(2,5-diaminophenoxy)-3,5-dioxaoctane and their addition salts with an acid.

N,N'-Bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred among these double bases of formula (II).

The para-aminophenols which can be used in the context of the invention can be chosen in particular from the compounds corresponding to the following formula (III) and their addition salts with an acid:

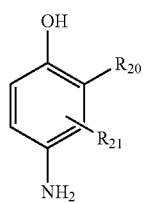

(III)

in which:
- $R_{20}$ represents a hydrogen atom, a halogen atom, such as fluorine, a $C_1$-$C_4$ alkyl radical, a $C_1$-$C_4$ monohydroxyalkyl radical, a ($C_1$-$C_4$)alkoxy($C_1$-$C_4$)alkyl radical, a $C_1$-$C_4$ aminoalkyl radical or a hydroxy($C_1$-$C_4$)alkylamino-($C_1$-$C_4$)alkyl radical,
- $R_{21}$ represents a hydrogen atom, a halogen atom, such as fluorine, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical, a $C_1$-$C_4$ cyanoalkyl radical or a ($C_1$-$C_4$)alkoxy($C_1$-$C_4$)alkyl radical.

Among the preferred para-aminophenols, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, N-methyl-para-aminophenol, and the acid addition salts thereof.

The ortho-aminophenols that may be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Among the heterocyclic bases that can be used as oxidation bases in the dye compositions in accordance with certain embodiments, mention may be made of pyridine derivatives, pyrimidine derivatives, pyrazole derivatives, pyrazolinone derivatives, and the acid addition salts thereof.

Among the pyridine derivatives, mention may be made of the compounds described, for example, in patents GB 1,026,978 and GB 1,153,196, as well as the compounds 2,5-diaminopyridine, 2-(4-methoxyphenyl)amino-3-aminopyridine, 2,3-diamino-6-methoxypyridine, 2-(β-methoxyethyl)amino-3-amino-6 methoxypyridine, 3,4-diaminopyridine, and the acid addition salts thereof.

Among the pyrimidine derivatives, mention may be made of the compounds disclosed, for example, in German Patent DE 2 359 399 or Japanese Patents JP 88-169 571 and JP 91-10659 or Patent Application WO 96/15765, such as 2,4,5,6-tetra-aminopyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-triaminopyrimidine, and the pyrazolopyrimidine derivatives, such as those mentioned in French Application FR-A-2 750 048 and among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethyl-pyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-(imidazolylpropylamino)pyrazolo[1,5-a]pyrimidine; and their addition salts and their tautomeric forms, when there exists a tautomeric equilibrium, and their addition salts with an acid.

Among the pyrazole and pyrazolinone derivatives, mention may be made the compounds described in patents DE 3,843,892, DE 4,133,957 and patent applications WO 94/08969, WO 94/08970, FR-A-2,733,749, and DE 195 43 988, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethyl-pyrazole, triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, 2-(4,5-diamino-1H-pyrazol-1-yl), $H_2SO_4$, 2,3-diamino-6,7-dihydro-1H,5H-pyrazolo[1,2-z] pyrazol-1-one, 1-methyl-3-phenyl-2-pyrazolinone, and the acid addition salts thereof.

Preferred primary intermediates are p-phenylenediamine, p-aminophenol, o-aminophenol, N,N-bis(β-hydroxyethyl)-p-phenylenediamine, 2,5-diaminotoluene, their salts and mixtures thereof.

The primary intermediates may be employed in amounts ranging from 0.0001% to 12% by weight, preferably from 0.0001% to 8.0% by weight, more preferably, from 0.005% to 5% by weight, based on the total weight of the color base composition.

B. Color Couplers

The color base composition of the present invention may also contain coupler compounds. The couplers that may be used in the dyeing method disclosed herein include those conventionally used in oxidation dye compositions, that is to say, meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and the acid addition salts thereof.

Suitable color couplers include, for example, those having the general formula (IV):

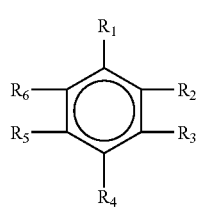

(IV)

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Other couplers may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, 6-methyl pyrazolo[1,5-a]-benzimidazole, and the acid addition salts thereof.

Preferred couplers include resorcinol, 1-naphthol, 2-methylresorcinol, 4-amino-2-hydroxy toluene, m-aminophenol, 2,4-diaminophenoxyethanol, phenyl methyl pyrazolone, hydroxybenzomorpholine, 2-methyl-5-hydroxyetyylaminophenol, 6-hydroxyindole, 2-amino-3-hydroxypyridine, 5-amino-6-chloro-o-cresol, 4-chlororesorcinol, their salts, and mixtures thereof.

When they are present, these couplers may be present in amounts ranging from 0.0001% to 12% by weight; preferably from 0.001% to 8% by weight, based on the total weight of the color base composition.

In general, the acid addition salts of the oxidation bases and couplers may be chosen from hydrochlorides, hydrobromides, sulphates, tartrates, lactates, and acetates.

C. Cosmetically Acceptable Medium

The color base composition of the invention can also comprise at least one solvent chosen from water, organic solvents and mixtures thereof.

Preferably, the color base composition of the present invention comprises at least __5_% by weight, more preferably at least 20_% by weight, and even more preferably at least __ 30_% by weight of water, based on the total weight of said color base composition.

According to a preferred embodiment, the color base composition comprises water and at least one co-solvent chosen from organic solvents.

Suitable organic solvents include alcohols, such as ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, polybutene, hydrogenated polyisobutene, hydrogenated polydecene, polydecene, squalene, petrolatum and isoparaffins; and mixtures, thereof.

The at least one co-solvent may be present in an amount ranging from about 1% to about 30% by weight, such as from about 2% to about 20% by weight, relative to the total weight of the color base composition.

Preferably, the color base composition of the present invention has a pH ranging from 2 to 12, more preferably from 3 to 11, and even more preferably from 6 to 10.

If necessary, suitable pH adjusters may be used to obtain the above-disclosed pH values. Examples of suitable pH adjusters include, but are not limited to, monoethanolamine, ammonium hydroxide, sodium hydroxide, arginine, aminomethyl propanol.

D. Optional Ingredients

The color base composition of the invention can also optionally contain other types of colorants. Suitable hair colorants include, but are not limited to, pigments, liposoluble dyes, direct dyes, nacreous pigments, pearling agents, leuco dyes, optical lightening colorants, natural colorants and optically-variable pigments.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, DC Blue No. 14, annatto, and quinoline yellow. The liposoluble dyes, when present, may have a concentration ranging up to 20% by weight of the total weight of the color base composition, such as from 0.0001% to 6% by weight.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the color base composition in a concentration ranging up to 50% by weight of the total weight of the color base composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, silica, ferric blue, and mixtures thereof. Representative examples of organic pigments include carbon black, pigments of D & C type, and lakes based on cochineal carmine, barium, strontium, calcium, and aluminum. Other examples of pigments are ultramarines, HC Blue No. 14, Ext. Yellow 7, Yellow 10 Lake, and acid violet 43.

If present, the pigments may be present in the composition in a concentration ranging up to 50% by weight of the total weight of the color base composition, such as from 0.5% to 40%, and further such as from 2% to 30%.

A direct dye is a colored substance that does not require the use of an oxidizing agent in order to reveal its color. Suitable direct dyes which may be used according to the present invention may be chosen from acidic (anionic), basic (cationic), and neutral dyes.

"Acidic dye" is generally intended to mean a dye containing at least one COOH, $SO_3H$, $PO_5H$, or $PO_4H_2$ group, it being possible for said groups to exist in the form of salts. "Salts" is generally intended to mean salts of metals (for example, alkali metals or alkaline earth metals), salts of an organic amine that is optionally hydroxylated. Such dyes are also referred to as anionic dyes.

The acidic dyes that can be used in the context of this invention can be chosen from acidic nitro dyes, acidic azo dyes, acidic amine dyes, acidic triarylmethane dyes, acidic quinone dyes, acidic indo-amine dyes and acidic natural dyes, and mixtures thereof.

"Basic dyes" is generally intended to mean a dye that has at least one group bearing a positive charge, such as an ammonium group or a quaternized nitrogen atom in a ring. Such dyes are also referred to as cationic dyes.

The basic dyes that can be used in the context of this invention can be chosen from nitrobenzene dyes, azo dyes, azomethine dyes, methine dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylamethane-derived dyes and basic natural dyes, and mixtures thereof.

Preferably, the direct dyes may be present in amounts ranging from 0.001% to 30% by weight, preferably from 0.01% to 20% by weight, more preferably from 0.1% to 10% by weight, based on the total weight of the color base composition.

Representative leuco dyes include those disclosed in US patent application publication no. 20040194231, the entire contents of which is hereby incorporated by reference. Leuco dyes are usually only slightly colored or are not colored at all and can be converted by simple oxidation in air or in the presence of an oxidizing agent into a triheteroylmethane compound. Examples of leuco dyes and corresponding triheteroylmethane compounds include 1H-Benzo[ij]quinolizinium, 9-[bis(2,3,6,7-tetrahydro-1H,5H-benzo[ij-]quinolizin-9-yl)methylene]-2,3,5,6,7,9-hexahydro-chloride; 5H-Benzo[a]carbazolium, 11-ethyl-5-[(11-ethyl-11H-benzo[a]carbazol-5-yl)(1-ethyl-1,2,3,4-tetrahydro-5-quinolinyl)methylene]-; Pyrrolo[3,2,1-ij]quinolinium, 8-[bis(1,2,5,6-tetrahydro-4H-pyrrolo[-3,2,1-ij]quinolin-8-yl)methylene]-1,2,4,5,6,8-hexahydro-; Tri(9-ethy-9H-carbazol-3-yl)methane; bis(6-Chloro-9-ethy-9H-carbazol-3-yl)-(9-ethy-9H-carbazol-3-yl)methane; bis(1-(4-sulfo-butyl)-2,3,4,6- tetrahydro-quinolinium)-pyrid-4-yl-methane; bis(1-ethyl-2-methyl-1H-indol-3-yl)-(9-ethy-9H-carbazol-3-yl)methane; Tri(7-ethyl-7H-benzo[c]carbazol-10-yl)methane; bis((6-dimethylamino-3-methyl-1H-indol-2-yl)-2-furylmethane; bis((6-dimethylamino-3-methyl-1H-indol-2-yl)-(pyrid-4-yl) methane; bis(1-ethyl-2-methyl-1H-indol-3-yl)-2-thienyl-methane; 3-[(1-ethyl-2-methyl-1H-indol-3-yl)-(9-ethy-9H-carbazol-3-yl)methylene]-1-ethyl-2-methyl-3H-indolium; and 3-[(1-ethyl-2-methyl-1H-indol-3-yl)-2-thienyl)methylene]-1-ethyl-2-methyl-3H-indolium.

Representative optical lightening colorants include those disclosed in US patent application publication no. US20040205905, the entire contents of which is hereby incorporated by reference.

Representative natural colorants include those disclosed in US patent application publication no. US20030159221, the entire contents of which is hereby incorporated by reference. For the purposes of the invention, the expression "natural colorant" means compounds that exist in nature, whether they have been obtained by extraction or reproduced chemically. Examples of natural direct dyes that may be used according to the invention include lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes and especially henna-based poultices or extracts.

2. Developer Composition

The developer composition of the invention comprises, in a medium suitable for dyeing, at least one oxidizing agent present in an amount sufficient to develop a coloration. The oxidizing agents employed in this invention is selected from persulfates, perborates, percarbonates, their salts, and mixtures thereof.

Preferred persulfates are monopersulfates such as, for example, potassium persulfate, sodium persulfate, ammonium persulfate, as well as mixtures thereof.

The preferred oxidizing agents in the present invention are potassium persulfate, sodium persulfate and mixtures thereof.

The at least one oxidizing agent is present in an amount sufficient to generate color in the hair without destroying the oxidative dye precursors which have migrated into the hair prior to completion of the hair dyeing process to the desired color/shade.

In general, the at least one oxidizing agent will be present in an amount of at least 1% by weight, based on the total weight of the developer composition.

According to a preferred embodiment, the at least one oxidizing agent is present in an amount ranging from 1% by weight to 80% by weight, preferably from 5% by weight to 75% by weight, based on the total weight of the developer composition.

Similarly, the developer composition is applied onto the hair for a period of time sufficient to generate color in the hair. In general, the developer composition is applied onto the hair for a period of from 1 to 20 minutes, such as from 1 to 10 minutes, for example from 1 to 5 minutes.

According to a first preferred embodiment of the invention, the developer composition is substantially anhydrous.

The term "substantially anhydrous" means that the developer composition is either completely free of water or contains no appreciable amount of water, preferably no more than 1% by weight, and more preferably no more than 0.5% by weight, based on the weight of the developer composition.

According to a particularly preferred embodiment of the invention, the developer composition is totally anhydrous, that is to say it does not contain water at all.

The developer composition can contain at least one solvent, chosen from water, organic solvents, and mixtures thereof.

When the developer composition is substantially anhydrous or totally anhydrous, the at least one solvent is chosen from organic solvents.

Suitable organic solvents include ethanol, isopropyl alcohol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, hydrocarbons such as straight chain hydrocarbons, mineral oil, polybutene, hydrogenated polyisobutene, hydrogenated polydecene, polydecene, squalane, petrolatum isoparaffins, and mixtures, thereof.

The at least one solvent may, for example, be present in an amount ranging from 0.5% to 70% by weight, such as from 2% to 60% by weight, preferably from 5 to 50% by weight, relative to the total weight of the developer composition.

The developer composition may be in the form of a powder, gel, liquid, foam, lotion, cream, mousse, and emulsion.

It should be noted that the use of a catalyst during the oxidation of the oxidative dye precursor such as, for example, cupric or ferrous salt, is not necessary in order to achieve a desired color/shade.

Thus, according to a preferred embodiment of the present invention, the color base composition and the developer composition of the present invention are substantially free of an oxidation catalyst, i.e., such catalyst is present in a less than catalytically effective amount in the color base and developer compositions.

As used herein, "oxidation catalyst" refers to transition metal cations that can aid in the oxidation of certain dye precursors, such as cupric and ferrous ions.

According to a particularly preferred embodiment, the color base composition and the developer composition are each totally free of cupric ions and of ferrous ions.

According to a particularly preferred embodiment, the color base composition and the developer composition do not contain hydrogen peroxide ($H_2O_2$).

The pH of the developer composition can range from 2 to 12, such as from 6 to 11, and it may be adjusted to the desired value using basifying/alkalizing agents that are well known in the art in the dyeing of keratin fibers.

3. Additional Ingredients

The described embodiments of the present invention may also include one or more additional ingredients, which may be incorporated into the color base composition, the developer composition, or both. Such ingredients include well-known conventional additives typically employed in hair coloring compositions such as basifying and acidifying agents, buffers, rheological modifiers, conditioning agents, surfactants, antioxidants, fragrances, and chelating agents.

A. Basifying Agents

Basifying (also called alkalizing) and acidifying agents may be used in the color base composition and in the developer composition.

Examples of the basifying or alkalizing agents include ammonia, alcanolamines such as monoethanolamine, diethanolamine, triethanolamine, isopropanolamine, propane-1,3-diamine, oxyethylenated and oxypropylenated hydroxyalkylamines and ethylenediamines, polyamines, sodium hydroxide and potassium hydroxide, ammonium or alkali carbonates, ammonium or alkali bicarbonates, alkali metal carbonates, alkali silicates, alkali metasilicates, organic carbonates, alkali hydroxides, aminomethylpropanol, and mixtures thereof.

The basifying agents may, for example, be present in an amount ranging from 0.05% to 40% by weight, relative to the total weight of the color base composition and/or the developer composition.

The basifying agents can also be used in the invention to adjust the pH of the color base composition and/or the developer composition.

B. Rheological Modifiers

According to the invention, the color base composition and/or the developer composition may also comprise at least one rheology modifier chosen from nonionic, anionic, cationic or amphoteric polymers, and other rheology modifiers such as cellulose-based thickeners (hydroxyethylcellulose, hydroxypropylcellulose, carboxymethylcellulose, cationic cellulose ether derivatives, quaternized cellulose derivatives, etc.), guar gum and its derivatives (hydroxypropyl guar, cationic guar derivatives, etc.), gums of microbial origin (xanthan gum, scleroglucan gum, etc.), crosslinked homopolymers of acrylic acid or of acrylamidopropanesulfonic acid and associative polymers as described below.

In particular, the color base composition and/or the developer composition may comprise at least one polymer chosen from nonionic, anionic, cationic or amphoteric amphiphilic polymers.

The amphiphilic polymers may contain a hydrophobic chain that is a saturated or unsaturated, aromatic or non-aromatic, linear or branched $C_6$-$C_{30}$ hydrocarbon-based chain, optionally comprising one or more oxyalkylene (oxyethylene and/or oxypropylene) units.

Among the cationic amphiphilic polymers comprising a hydrophobic chain that may be found are cationic polyurethanes or cationic copolymers comprising vinyllactam units and in particular vinylpyrrolidone units.

As examples of nonionic amphiphilic polymers containing a hydrophobic chain, mention may be made, inter alia, of:

(1) celluloses modified with groups comprising at least one saturated or unsaturated, linear or branched $C_6$-$C_{30}$ hydrocarbon-based chain, for instance hydroxyethylcelluloses modified with groups comprising at least one hydrophobic chain as defined previously, such as especially Natrosol Plus Grade 330 CS ($C_{16}$ alkyls—sold by the company Aqualon); Bermocoll EHM 100 (sold by the company Berol Nobel), Amercell Polymer HM-1500 (hydroxyethylcellulose modified with a polyethylene glycol (15) nonylphenyl ether group—sold by the company Amerchol);

(2) hydroxypropyl guars modified with groups comprising at least one hydrophobic chain as defined, for example Jaguar XC-95/3 ($C_{14}$ alkyl chain—sold by the company Rhodia Chimie); Esaflor HM 22 ($C_{22}$ alkyl chain—sold by the company Lamberti); RE210-18 ($C_{14}$ alkyl chain) and RE205-1 ($C_{20}$ alkyl chain) sold by the company Rhodia Chimie;

(3) copolymers of vinylpyrrolidone and of hydrophobic monomers containing a hydrophobic chain as defined above, for instance Antaron or Ganex V216 (vinylpyrrolidone/hexadecene copolymers); Antaron or Ganex V220 (vinylpyrrolidone/eicosene copolymers), sold by the company I.S.P.;

(4) copolymers of $C_1$-$C_6$ alkyl(meth)acrylates and of amphiphilic monomers containing a hydrophobic chain;

(5) copolymers of hydrophilic(meth)acrylates and of hydrophobic monomers comprising at least one hydrophobic chain, for instance the polyethylene glycol methacrylate/lauryl methacrylate copolymer;

(6) polymers with an aminoplast ether skeleton containing at least one fatty chain, such as the Pure Thix compounds sold by the company Sud-Chemie;

(7) linear (block structure), grafted or starburst polyurethane polyethers comprising in their chain at least one hydrophilic block, which is generally a polyoxyethylene block which may comprise between 50 and 1 000 oxyethylene units approximately, and at least one hydrophobic block, which may comprise aliphatic groups alone, optionally combined with cycloaliphatic and/or aromatic blocks. Preferably, the polyurethane polyethers comprise at least two $C_6$-$C_{30}$ hydrocarbon-based hydrophobic chains, separated by a hydrophilic block; the hydrophobic chains may be pendent chains or chains with one or more of the end groups of the hydrophilic block(s).

The polyurethane polyethers comprise a urethane bond between the hydrophilic blocks, but may also contain hydrophilic blocks linked to the lipophilic blocks via other chemical bonds.

Examples of polyurethane polyethers that may be mentioned include Nuvis FX 1100 (European and US INCI name "Steareth-100/PEG-136/HMDI Copolymer" sold by the company Servo Delden); Rheolate 205, 208, 204 or 212 (sold by the company Rheox); Elfacos T210 ($C_{12}$-$C_{14}$ alkyl chain) and Elfacos T212 ($C_{18}$ alkyl chain) sold by the company Akzo.

The anionic amphiphilic polymers containing a hydrophobic chain that may be used comprise, as hydrophobic chain, at least one saturated or unsaturated, aromatic or non-aromatic, linear or branched $C_8$-$C_{30}$ hydrocarbon-based chain.

More particularly, the anionic amphiphilic polymers comprising at least one hydrophobic chain which are crosslinked or non-crosslinked, comprise at least one hydrophilic unit derived from one or more ethylenically unsaturated monomers bearing a carboxylic acid function, or a sulphonic function which is free or partially or totally neutralized, and at least one hydrophobic unit derived from one or more ethylenically unsaturated monomers bearing a hydrophobic side chain, and optionally at least one crosslinking unit derived from one or more polyunsaturated monomers.

The amphiphilic polymers may also comprise at least one sulphonic group, in free or partially or totally neutralized form and at least one hydrophobic portion.

Among these, mention may be made more particularly of acrylamido-2-methyl-2-propanesulphonic (AMPS) acid/n-dodecylacrylamide copolymer neutralized with sodium hydroxide, the copolymer crosslinked with methylenebisacrylamide consisting of 75% by weight of AMPS units neutralized by $NH_3$ and 25% by weight of Genapol T-250 acrylate units, the copolymer crosslinked with allyl methacrylate consisting of 90% by weight of AMPS units neutralized with $NH_3$ and 10% by weight of Genapol T-250 methacrylate units, or the copolymer crosslinked with allyl methacrylate consisting of 80% by weight of AMPS units neutralized with $NH_3$ and 20% by weight of Genapol T-250 methacrylate units.

Other examples include Carbopol ETD-2020 (acrylic acid/$C_{10}$-$C_{30}$ alkyl methacrylate crosslinked copolymer sold by the company Noveon); Carbopol 1382, Pemulen TR1 and Pemulen TR2 (acrylic acid/$C_{10}$-$C_{30}$ alkyl acrylate crosslinked copolymers—sold by the company Noveon), the methacrylic acid/ethyl acrylate/oxyethylenated stearyl methacrylate copolymer (55/35/10); the (meth)acrylic acid/ethyl acrylate/25 EO oxyethylenated behenyl methacrylate copolymer (Aculyn 28 sold by Rohm & Haas) and the methacrylic acid/ethyl acrylate/steareth-10 allyl ether crosslinked copolymer.

When the developer composition comprises one or more amphiphilic polymer(s) containing a hydrophobic chain, then this or these polymer(s) generally represent(s) from 0.01% to 20% by weight and preferably, from 0.05% to 10% by weight of the total weight of this composition.

The rheology modifier(s) that may be present in the developer composition is (are) polymers of natural origin or synthetic polymers, and are advantageously chosen from those conventionally used in cosmetics.

Examples of synthetic polymers that may be mentioned include polyvinylpyrrolidone, polyacrylic acid, polyacrylamide, non-crosslinked poly(2-acryl-amidopropanesulphonic acid) (Simugel EG from the company SEPPIC), crosslinked poly(2-acrylamido-2-methylpropanesulphonic acid), free or partially neutralized with ammonia (Hostacerin AMPS from Clariant), mixtures of non-crosslinked poly(2-acrylamido-2-methylpropanes-sulphonic acid) with hydroxyalkylcellulose ethers or with poly(ethylene oxide)s, as described in patent U.S. Pat. No. 4,540,510; mixtures of poly((meth)acrylamido ($C_1$-$C_4$)alkylsulphonic acid), which is preferably crosslinked, with a crosslinked copolymer of maleic anhydride and of a ($C_1$-$C_5$)alkyl vinyl ether (Hostacerin AMPS/Stabileze QM from the company ISF).

The thickening polymers of natural origin are preferably polymers comprising at least one sugar unit, for instance nonionic guar gums, optionally modified with $C_1$-$C_6$ hydroxyalkyl groups; biopolysaccharide gums of microbial origin, such as scleroglucan gum or xanthan gum; gums derived from plant exudates, such as gum arabic, ghatti gum, karaya gum, gum tragacanth, carrageenan gum, agar gum and carob gum; pectins; alginates; starches; hydroxy($C_1$-$C_6$)alkylcelluloses and carboxy($C_1$-$C_6$)alkylcelluloses.

It should be noted that the term "sugar unit" denotes a monosaccharide (i.e. monosaccharide or oside or simple sugar) portion, an oligosaccharide portion (short chains formed from a sequence of monosaccharide units, which may be different) or a polysaccharide portion [long chains consisting of monosaccharide units, which may be different, i.e. polyholosides or polyosides]. The saccharide units may also be substituted with alkyl, hydroxyalkyl, alkoxy, acyloxy or carboxyl radicals, the alkyl radicals containing from 1 to 4 carbon atoms.

Examples of nonionic, unmodified guar gums that may be mentioned, inter alfa, include Guargel D/15 (Noveon); Vidogum GH 175 (Unipectine), Meypro-Guar 50 and Jaguar C (Meyhall/Rhodia Chimie); and the modified nonionic guar gums that may be mentioned include Jaguar HP8, HP60, HP120, DC 293 and HP 105 (Meyhall/Rhodia Chimie); Galactasol 4H4FD2 (Aqualon).

The biopolysaccharide gums of microbial or plant origin are well known to those skilled in the art and are described especially in the book by Robert L. Davidson entitled "Handbook of Water soluble gums and resins" published by McGraw Hill Book Company (1980).

Among these gums, mention will be made of scleroglucans such as, especially, Actigum CS from Sanofi Bio Industries; Amigel from Alban Muller International, and also the glyoxal-treated scleroglucans described in FR 2 633 940); xanthan gums, for instance Keltrol, Keltrol T, Keltrol Tf, Keltrol Bt, Keltrol Rd, Keltrol Cg (Nutrasweet Kelco), Rhodicare S and Rhodicare H (Rhodia Chimie); starch derivatives, for instance Primogel (Avebe); hydroxyethylcelluloses such as Cellosize QP3L, QP4400H, QP30000H, HEC30000A and Polymer PCG10 (Amerchol), Natrosol 250HHR, 250MR, 250M, 250HHXR, 250HHX, 250HR, HX (Hercules) and Tylose H1000 (Hoechst); hydroxypropylcelluloses, for instance Klucel EF, H, LHF, MF and G (Aqualon); carboxymethylcelluloses, for instance Blanose 7M8/SF, refined 7M, 7LF, 7MF, 9M31F, 12M31XP, 12M31P, 9M31XF, 7H, 7M31, 7H3SXF (Aqualon), Aquasorb A500 (Hercules), Ambergum 1221 (Hercules), Cellogen HP810A, HP6HS9 (Montello) and Primelose (Avebe).

When the color base composition and/or the developer composition comprises one or more rheology modifiers, then this or these agent(s) generally represent(s) from 0.01% to 20% by weight and better still from 0.05% to 10% by weight of the total weight of this composition.

E. Conditioning Agents

The color base and/or the developer compositions of the present invention may also contain at least one conditioning agent. Such conditioning agents are typically chosen from synthetic oils such as polyolefins, plant oils, fluoro oils or perfluoro oils, natural or synthetic waxes, silicones, non-polysaccharide cationic polymers, compounds of ceramide type, cationic surfactants, fatty amines, fatty acids and derivatives thereof, and also mixtures of these various compounds. Other useful conditioning agents are conditioning polymers which contain primary, secondary, tertiary and/or quaternary amine groups, forming part of the polymer chain or linked directly to the latter, and having a molecular weight of between 500 and approximately 5,000,000, and preferably between 1000 and 3,000,000.

Among these polymers, there may be mentioned, more especially, quaternized proteins, polymers of the polyamine, polyaminoamide or poly(quaternary ammonium) family and cationic polysiloxanes.

The quaternized proteins are, in particular, chemically modified polypeptides bearing quaternary ammonium groups at the end of the chain or grafted onto the latter.

Among the polyamine, polyaminoamide or poly(quaternary ammonium) family of polymers, there may be mentioned:

1) Vinylpyrrolidone/dialkylaminoalkyl acrylate or methacrylate copolymers, quaternized or otherwise, such as the products sold by the company GAF CORPORATION under the name "GAFQUAT", for example "GAFQUAT 734 or 755", or alternatively the products designated "COPOLYMER 845, 958 and 937".

2) The cellulose ether derivatives containing quaternary ammonium groups, especially the polymers marketed by the company UNION CARBIDE CORPORATION under the names "JR" (JR 400, JR 125, JR 30M) or "LR" (LR 400, LR 30M). The polymers are also defined in the CTFA Dictionary as quaternary ammonium derivatives of hydroxyethylcellulose subjected to reaction with an epoxide substituted with a trimethylammonium group.

3) Cationic cellulose derivatives such as cellulose copolymers or cellulose derivatives grafted with a water-soluble quaternary ammonium monomer such as, for example hydroxyalkylcelluloses such as hydroxymethyl-, hydroxyethyl- or hydroxypropylcellulose grafted with a methacryloylethyltrimethylammonium, methacrylamidopropyltrimethylammonium or dimethyldiallylammonium salt.

Marketed products corresponding to this definition are, more especially, the products sold by the company NATIONAL STARCH under the names "CELQUAT L 200" and "CELQUAT H 100".

4) The quaternized polysaccharides marketed under the name "JAGUAR C 13 S", sold by the company MEYHALL.

5) Cyclopolymers having a molecular weight of 20,000 to 3,000,000 such as, for example, the homopolymer of dimethyldiallylammonium chloride sold by the company MERCK under the name "MERQUAT 100", having a molecular weight of less than 100,000, and the copolymer of dimethyldiallylammonium chloride and acrylamide having a molecular weight above 500,000 and sold under the name "MERQUAT 550".

6) Quaternary polymers of vinylpyrrolidone and of vinylimidazole, such as, for example, the products marketed by the company BASF under the names "LUVIQUAT FC 905, FC 550 and FC 370".

Other conditioning polymers which are usable according to the invention are polyalkylenimines, especially polyethylenimines, polymers containing vinylpyridine or vinylpyridinium units, condensates of polyamines and epichlorohydrin, quaternary polyureylenes and chitin derivatives.

The cationic polysiloxanes such as those described in U.S. Pat. No. 4,185,087.

The conditioning polymers may also be chosen from amphoteric polymers, such as amphoteric polymers derived from chitosan or copolymers of diallyldialkylammonium and an anionic monomer.

Preferred polymers are, inter alia, polymers containing alkyl groups chosen from groups having 1 to 4 carbon atoms, and more especially methyl and ethyl groups.

Especially preferred conditioning polymers according to the invention are chosen from:
a) the poly(quaternary ammonium) polymers;
b) the copolymer of the diallyldimethylammonium chloride and acrylic acid (80/20) sold by the company CALGON under the name MERQUAT 280;
c) the homopolymer of dimethyldiallylammonium chloride sold by the company MERCK under the name MERQUAT 100;
d) the quaternized cellulose ether derivatives sold by the company UNION CARBIDE under the name JR;
e) the copolymer of vinylpyrrolidone and methacrylamidopropyltrimethylammonium chloride (85:15) sold by the company GAF under the name GAFQUAT HS 100;
f) the polymeric quaternary ammonium salt of acrylamide and beta-methacrylyloxyethyl trimethyl ammonium methosulfate, sold by the company, Nalco, under the names polyquaternium-5 or quaternium-39 or Merquat 5; and
g) the cationic polymers of the ionene type sold by the company Chimex, such as hexadimethrine chloride, also known as IONENE G.

According to a preferred embodiment, the color base composition contains at least one conditioning agent as defined above. More preferably, the color base composition contains at least one conditioning polymer, in an amount of from 0.01% to 12% by weight, preferably from 0.1 to 10% by weight, more preferably from 0.1 to 8% by weight, all weights being based on the total weight of the color base composition.

F. Surfactants

The color base composition and/or the developer composition may also contain at least one surfactant, chosen from anionic, amphoteric, non-ionic, zwitterionic and cationic surfactants, and mixtures thereof.

The at least one surfactant may be chosen, for example, from the following:

(i) Anionic Surfactant(s):

The color base composition and/or the developer composition may contain at least one anionic surfactant chosen, for example, from salts (for example, alkali metal salts, such as sodium salts, ammonium salts, amine salts, amino alcohol salts and magnesium salts) of the following compounds: alkyl sulphates, alkyl ether sulphates, alkylamino ether sulphates, alkylarylpolyether sulphates, monoglyceride sulphates; alkyl sulphonates, alkyl phosphates, alkyl amide sulphonates, alkyl aryl sulphonates, α-olefin sulphonates, paraffin sulphonates; ($C_6$-$C_{24}$)alkyl sulphosuccinates, ($C_6$-$C_{24}$)alkyl ether sulphosuccinates, ($C_6$-$C_{24}$)alkyl amide sulphosuccinates; ($C_6$-$C_{24}$) alkyl sulphoacetates; ($C_6$-$C_{24}$)acryl sarcosinates; and ($C_6$-$C_{24}$)acryl glutamates. At least one anionic surfactant may also be chosen, for example, from ($C_6$-$C_{24}$)alkylpolyglycoside carboxylic esters, such as alkylglucoside citrates, alkylpolyglycoside tartrates and alkylpolyglycoside sulphosuccinates, alkylsulphosuccinamates; acyl isethionates and N-acyl taurates, alkyl radicals and acyl radicals of these different compounds, such as those comprising from 12 to 20 carbon atoms, and at least one aryl radical may be chosen, for example, from phenyl and benzyl groups. At least one anionic surfactant may be chosen, for example, from fatty acid salts, such as oleic, ricinoleic, palmitic and stearic acid salts, coconut oil acid and hydrogenated coconut oil acid; acyl lactylates wherein the acyl radical comprises 8 to 20 carbon atoms. At least one anionic surfactant may be chosen, for example, from alkyl D-galactoside uronic acids and their salts, polyoxyalkylenated($C_6$-$C_{24}$)alkyl ether carboxylic acids, polyoxyalkylenated ($C_6$-$C_{24}$)alkyl aryl ether carboxylic acids, polyoxyalkylenated($C_6$-$C_{24}$)alkylamido ether carboxylic acids and their salts, for example, those comprising from 2 to 50 alkylene oxide groups, such as ethylene oxide groups, and mixtures thereof.

(ii) Non-Ionic Surfactant(s):

The color base composition and/or the developer composition may contain at least one non-ionic surfactant chosen, for example, from non ionic surfactants compounds disclosed in "Handbook of Surfactants" by M. R. Porter, published by Blackie & Son (Glasgow and London), 1991, pp. 116-178. The at least one non-ionic surfactants may be chosen, for example, from polyethoxylated and/or polypropoxylated alkyl phenols, alpha-diols and alcohols, comprising fatty chains comprising, for example, from 8 to 18 carbon atoms, and the number of ethylene oxide and/or propylene oxide groups may range from 2 to 50. The at least one non-ionic surfactant may be chosen, for example, from copolymers of ethylene oxide and of propylene oxide, condensates of ethylene oxide and/or of propylene oxide with fatty alcohols; polyethoxylated fatty amides comprising, for example, from 2 to 30 mol of ethylene oxide, polyglycerolated fatty amides comprising on average 1 to 5, and, for example, 1.5 to 4, glycerol groups; polyethoxylated fatty amines comprising, for example, from 2 to 30 mol of ethylene oxide; oxyethylenated fatty acid esters of sorbitan comprising, for example, from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$-$C_{14}$)alkyl amine oxides and N-acylaminopropylmorpholine oxides.

(iii) Amphoteric or Zwitterionic Surfactant(s):

The color base composition and/or the developer composition may contain at least one amphoteric or zwitterionic surfactant that may be chosen, for example, from aliphatic secondary and tertiary amine derivatives wherein the aliphatic radical comprises linear and branched chains comprising 8 to 18 carbon atoms and comprising at least one water-solubilizing anionic group (for example, carboxylate, sulphonate, sulphate, phosphate and phosphonate); and ($C_8$-$C_{20}$)alkylbetaines, sulphobetaines, ($C_8$-$C_{20}$)alkylamido($C_1$-$C_6$)alkylbetaines and ($C_8$-$C_{20}$)alkylamido($C_1$-$C_6$)alkylsulphobetaines.

At least one amine derivative may be chosen, for example, from the products sold under the name Miranol, described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

wherein: $R_2$ is chosen from alkyl radicals of acids of formula $R_2$—COOH which are present in hydrolysed coconut oil, heptyl, nonyl and undecyl radicals; $R_3$ is chosen from beta-hydroxyethyl groups and $R_4$ is chosen from carboxymethyl groups; and

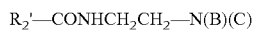

wherein:

B is chosen from —$CH_2CH_2OX'$; C is chosen from —$(CH_2)_z$—Y', wherein z=1 or 2, X' is chosen from the —$CH_2CH_2$—COOH group and a hydrogen atom, Y' is chosen from —COOH and the —$CH_2$—CHOH—$SO_3H$ radical, $R_2'$ is chosen from alkyl radicals of acids $R_9$—COOH present in coconut oil and in hydrolysed linseed oil, alkyl radicals, such as $C_7$, $C_9$, $C_{11}$ and $C_{13}$ alkyl radicals, $C_{17}$ alkyl radicals and its is to form, and unsaturated $C_{17}$ radicals.

These compounds are classified, for example, in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

Mention may be made of the cocoamphodiacetate sold, for example, under the trade name Miranol® C2M concentrate by the company Rhodia Chimie.

(iv) Cationic Surfactant(s):

The color base composition and/or the developer composition may contain at least one cationic surfactant chosen, for example, from: salts of optionally polyoxyalkylenated primary, secondary and tertiary fatty amines; quaternary ammonium salts such as tetra alkyl ammonium, alkylamidoalkyltrialkyl ammonium, trialkylbenzyl ammonium, trialkylhydroxyalkyl ammonium and alkylpyridinium chlorides and bromides; imidazoline derivatives; and cationic amine oxides.

The at least one surfactant may be present in the color base and/or in the developer composition, in an amount ranging from 0.01% to 40%, such as from 0.05% to 30%, relative to the total weight of each composition.

G. Chelating Agents

The color base composition and/or the developer composition of the present invention may also contain at least one chelating agent. Preferred ranges of chelating agent are from 0.001% to 5%, preferably from 0.005% to 4%, more preferably from 0.01 to 3% by weight of each composition. Preferred chelating agents are EDTA, HEDTA, and sodium or potassium salts, and mixtures, thereof.

H. Antioxidants and Reducing Agents

The color base composition and/or the developer composition of the present invention may also contain at least one antioxidant and/or reducing agent such as ascorbic acid, ascorbylated compounds, such as ascorbyl dipalmitate, t-butylhydroquinone, polyphenols, such as phloroglucinol, thiols, for example, cysteine, sodium sulfite, and sodium hydrosulfite, erythorbic acid, flavonoids, and mixtures thereof. Other examples of reducing agents that are useful include, but are not limited to: anhydrous sodium thiosulfate, powdered sodium metabisulfite, thiourea, ammonium sulfite, thioglycolic acid, thiolactic acid, ammonium thiolactate, glyceryl monothioglycolate, ammonium thioglycolate, thioglycerol, 2,5-dihydroxybenzoic acid, diammonium dithioglycolate, strontium thioglycolate, calcium thiolgycolate, zinc formosulfoxylate, isooctyl thioglycolate, and monoethanolamine thiogylcolate.

The antioxidant and/or reducing agent may be present in the color base composition in an amount ranging from 0.1% to 20% by weight relative to the total weight of the color base composition.

I. Other ingredients

The color base composition and/or the developer composition of the present invention can also comprise any additive typically used in cosmetic or hair treatment compositions. The additives may include waxes, organogelators, dispersants, oils, preserving agents, fragrances, fillers, neutralizing agents, hydroxy acids, UV filters, ceramides, pseudoceramides, vegetable, mineral oils, synthetic oils, vitamins, and provitamins.

Needless to say, a person skilled in the art will take care to select the optional additional compound(s) mentioned above such that the advantageous properties intrinsically associated with the dye composition disclosed herein are not, or are not substantially, adversely affected by the envisaged addition(s).

The main embodiment of this invention involves applying the color base composition onto the hair, followed by the application of the developer composition onto the hair, either immediately after application of the color base composition, or at any time thereafter that is convenient to the consumer from the time of application of the color base composition. According to a preferred embodiment, the developer composition is applied up to 60 minutes after application of the color base composition. The hair being colored may be dry, damp or wet.

It should be noted, however, that in between application of the color base composition and the developer composition, the hair may be rinsed in order to remove excess color base composition from the hair. The advantage of employing the rinsing step is that the oxidizing agent is then able to react more thoroughly with the oxidation dye precursor present in and around the hair shaft, thereby achieving enhanced fade resistance/less color loss properties.

Thus according to a particularly preferred embodiment of the present invention, the color base composition is rinsed off from the hair before the application of the developer composition.

Moreover, the oxidation dye precursors are, in general, colorless or weakly colored such that, in the event a rinsing step is employed in between application of the color base and developer compositions, the excess oxidation dye precursors are rinsed from the hair and scalp before application of the developer composition. This then allows the hair color to be formed only between the oxidation dye precursors that remain in and on the hair fibers and the oxidizing agent, thereby minimizing, and perhaps even eliminating, the problems of scalp staining and messy applications encountered with conventional hair dyes systems.

The present invention will be better understood from the examples which follow, all of which are intended for illustrative purposes only, and are not meant to unduly limit the scope of the invention in any way.

EXAMPLES

Example 1

ProcedureAccording to the Invention: The color base composition described hereunder was applied onto individual hair swatches, and allowed to remain in contact therewith for approximately 1 minute or 5 minutes. The hair swatches were then rinsed with water. The developer composition described hereunder was then applied onto the hair swatches, and the color was allowed to immediately develop in the hair. The developer composition was allowed to remain in contact with the hair for approximately 1 minute. The hair was then rinsed and dried.

Color base composition:

| Ingredients | Wt. % Formula A |
|---|---|
| Hexylene glycol | 5 |
| Trideceth-2 carboxamide MEA | 1 |
| Cetrimonium chloride | .008 |
| Aminomethyl propanol | 2.37 |
| Potassium sorbate | 0.1 |
| Trideceth-6 | 0.03936 |
| Sclerotium gum | 0.8 |
| N,N-bis(2-hydroxyethyl)-p-phenylenediamine sulfate | 1 |
| 2-oleamido-1,3-octadecanediol | 0.01 |
| Propylene glycol | 5 |
| 2,4-diaminophenoxyethanol HCl | 0.8 |
| Isopropyl alcohol | 0.18 |
| Amodimethicone | 0.46 |
| Behentrimonium chloride | 0.79 |
| Sodium metabisulfite | 0.7 |
| Erythorbic acid | 0.3 |
| Hydroxyethyl cellulose | 1 |
| Propylparaben | 0.2 |
| Methylparaben | 0.2 |
| Water | Up to 100 |
| pH of the color base composition | 9.6 |

Developer composition:

| Ingredients | Wt. % Formula B |
|---|---|
| Potassium persulfate | 27.50 |
| Sodium persulfate | 10.00 |
| Silica | 2.00 |
| Sodium metasilicate | 2.50 |
| Sodium silicate | 7.00 |
| EDTA | 1.00 |
| Tribehenin | 5.00 |
| Polydecene | 45.00 |

Comparative Procedure: The color base composition above was applied onto individual hair swatches, and allowed to remain in contact therewith for approximately 5 minutes. The hair swatches were then rinsed with water. A conventional developer composition consisting of an aqueous solution of hydrogen peroxide (hydrogen peroxide content of 20 volumes) as the oxidizing agent was then applied onto the hair swatches. The conventional developer composition was allowed to remain in contact with the hair swatches for approximately 1 minute. The hair was then rinsed and dried.

Colorimetric Results:

The color of hair swatches treated according to the inventive compositions and method and hair swatches treated with a conventional hair dye was measured using a Minolta CM2002 colorimeter in the L*a*b* system. In the L*a*b* system, the 3 parameters denote, respectively, the intensity or lightness of the color (L*), the value of the color on a green/red axis (a*) and the value of the color on a blue/yellow axis(b*). According to this system, the greater the value of L, the lighter or less intense the color. Conversely, the lower the value of L, the darker or more intense the color. Also, according to this system, the overall color change, LE, can be calculated from the $\Delta L$, $\Delta A$, and $\Delta B$ values. The benefits achieved by this invention are illustrated from the color deposit and shampoo test (fade resistance or color-fastness) data below. The hair used as a control was 90% grey chemically treated hair.

Color deposit results:

| Oxidant | Processing Time (for dyeing compositions) | L | $\Delta L$ |
|---|---|---|---|
| Persulfate-containing developer composition | 5 min | 44.92 | −20.69 |
| 20 Volume Hydrogen Peroxide Developer | 5 min | 51.13 | −14.48 |
| Persulfate-containing developer composition | 1 min | 50.28 | −15.33 |
| Untreated Hair | | 65.61 | |

For color deposit assessments, the $\Delta L$ or the difference between the L value for the dye-treated hair versus the L value for the control hair sample represents a change in the value of L: the more negative the $\Delta L$ value is, the greater the amount of color that is deposited onto the hair.

$$\Delta L = L_t(\text{dye-treated hair}) - L_c(\text{control, 90\% grey chemically treated hair}).$$

Therefore, it can be seen that greater color deposit was achieved using the persulfate-containing developer composition at 1 minute and at 5 minutes of processing as compared to using the conventional peroxide-containing developer composition at 5 minutes of processing time.

Example 2

The tables hereunder detail the composition of typical color base and developer compositions for use in the method of the present invention.

Color base composition

| Ingredients | Wt % |
|---|---|
| Deionized water | QS 100% |
| Sodium hydroxide | Qs pH = 9.6 |
| Pentasodium pentetate | 2.000 |
| Erythorbic acid | 0.300 |
| Sodium metabisulfite | 0.460 |
| Oxidative dyes | — |
| Cetearyl alcohol | 7.000 |
| Fragrance | 1.000 |
| Sclerotium gum | 0.800 |
| Chlorhexidine dihydrochloride | 0.050 |
| Methylparaben | 0.300 |
| Amodimethicone (and) trideceth-6 (and) cetrimonium chloride | 1.800 |

-continued

| Color base composition | |
|---|---|
| Ingredients | Wt % |
| Propylene glycol | 2.000 |
| Behentrimonium chloride | 4.000 |
| Cocamidopropyl betaine | 10.000 |
| | 100.00% |
| pH of the color base composition | 9.6 |

| Developer composition | |
|---|---|
| Ingredients | Wt % |
| Sodium persulfate | 75.000 |
| Silica | 23.300 |
| Polydecene | 1.700 |
| | 100.00% |

Method According to the Invention:

The color base composition described above is applied onto individual hair swatches, and allowed to remain in contact therewith for approximately 10 minutes. The hair swatches are then rinsed with water. The developer composition described above is then applied onto the hair swatches, and the color is allowed to immediately develop in the hair. The developer composition is allowed to remain in contact with the hair for approximately 5 minutes. The hair is then rinsed and dried.

The invention claimed is:

1. A method of permanently coloring hair comprising the steps of:
   (a) providing a color base composition containing at least one primary dye intermediate chosen from ortho aminophenols, para aminophenols, ortho phenylenediamines, para phenylenediamines, double bases, heterocyclic bases, the acid addition salts thereof, and mixtures thereof;
   (b) applying the color base composition onto the hair;
   (c) optionally, rinsing the color base composition from the hair;
   (d) providing a developer composition comprising at least one oxidizing agent chosen from persulfates, perborates, percarbonates, their salts, and mixtures thereof wherein the developer composition does not contain hydrogen peroxide; and
   (e) applying the developer composition onto the hair in order to develop a color, in situ, in the hair, the developer composition being applied up to 60 minutes after application of the color base composition.

2. The method of claim 1, wherein the color base composition and the developer composition are substantially free of an oxidation catalyst.

3. The method of claim 1, wherein the at least one oxidizing agent is chosen from monopersulfates.

4. The method of claim 3, wherein the at least one oxidizing agent is chosen from potassium persulfate, sodium persulfate, ammonium persulfate, and mixtures thereof.

5. The method claim 1, wherein the at least one oxidizing agent is present in an amount of at least 1% by weight, based on the total weight of the developer composition.

6. The method of claim 1, wherein the at least one oxidizing agent is present in an amount ranging from 1% by weight to 80% by weight, based on the total weight of the developer composition.

7. The method of claim 1, wherein the developer composition is substantially anhydrous.

8. The method of claim 1, wherein the color base composition is rinsed off from the hair before the application of the developer composition.

9. The method of claim 1, wherein the at least one oxidizing agent is chosen from persulfate salts and mixtures thereof.

10. The method of claim 1, wherein the at least one oxidizing agent is chosen from perborate salts and mixtures thereof.

11. The method of claim 1, wherein the at least one oxidizing agent is chosen from percarbonate salts and mixtures thereof.

12. The method of claim 1, wherein the pH of the color base composition and/or of the developer composition ranges from 2 to 12.

13. The method of claim 1, wherein the color base composition comprises at least 5% by weight of water, based on the total weight of said color base composition.

14. A kit for coloring a keratinous substrate comprising:
   (a) a multi-unit receptacle;
   (b) at least one unit comprising a color base composition, as defined in claim 1, which comprises at least one primary dye intermediate chosen from, ortho aminophenols, para aminophenols, ortho phenylenediamines, para phenylenediamines, double bases, heterocyclic bases, the acid addition salts thereof, and mixtures thereof; and
   (c) at least one unit comprising a developer composition, which comprises at least one oxidizing agent chosen from persulfates, perborates, percarbonates, their salts, and mixtures thereof wherein the developer composition does not contain hydrogen peroxide.

15. The method of claim 2, wherein the at least one oxidizing agent is chosen from monopersulfates.

16. The method of claim 2, wherein the at least one oxidizing agent is present in an amount of at least 1% by weight, based on the total weight of the developer composition.

17. The method of claim 3, wherein the at least one oxidizing agent is present in an amount of at least 1% by weight, based on the total weight of the developer composition.

18. The method of claim 4, wherein the at least one oxidizing agent is present in an amount of at least 1% by weight, based on the total weight of the developer composition.

19. The method of claim 2, wherein the at least one oxidizing agent is present in an amount ranging from 1% by weight to 80% by weight, based on the total weight of the developer composition.

* * * * *